United States Patent [19]

Lindsay

[11] Patent Number: 5,399,156
[45] Date of Patent: Mar. 21, 1995

[54] QUICK-CHANGEOVER BLOOD HANDLING APPARATUS

[75] Inventor: Erin J. Lindsay, Manchester, Mich.

[73] Assignee: Minnesota Mining and Manufacturing Company, St. Paul, Minn.

[21] Appl. No.: 77,344

[22] Filed: Jun. 14, 1993

Related U.S. Application Data

[63] Continuation-in-part of Ser. No. 898,491, Jun. 15, 1992, abandoned, which is a continuation-in-part of Ser. No. 493,286, Mar. 14, 1990, Pat. No. 5,149,318, and a continuation-in-part of Ser. No. 686,495, Apr. 7, 1991, Pat. No. 5,254,080, which is a continuation-in-part of Ser. No. 493,286, Mar. 14, 1990, Pat. No. 5,149,318.

[51] Int. Cl.⁶ .................................... B01D 19/02
[52] U.S. Cl. ........................ 604/4; 604/319; 604/405; 604/406
[58] Field of Search .......... 137/627.5, 625.13, 625.17, 137/625.18, 625.33, 625.25, 625.39; 604/905, 4, 5, 6, 317, 318, 319, 403, 405, 406

[56] References Cited

U.S. PATENT DOCUMENTS

| | | | |
|---|---|---|---|
| 3,585,995 | 6/1971 | Perkins et al. | 128/214 |
| 3,678,959 | 7/1972 | Liposky | 137/625.11 |
| 4,064,909 | 12/1977 | Neward | 137/625.48 |
| 4,224,958 | 9/1980 | Kaplan et al. | 137/625.13 X |
| 4,306,705 | 12/1981 | Svensson | 251/149.9 |
| 4,432,760 | 2/1984 | Mittleman et al. | 604/246 |
| 4,440,723 | 4/1984 | Gordon | 422/47 |
| 4,541,829 | 9/1985 | Munsch et al. | 604/29 X |
| 4,568,345 | 2/1986 | Keilman et al. | 604/403 |
| 4,576,199 | 3/1986 | Svensson et al. | 137/614.04 |
| 4,597,414 | 7/1986 | Johnson | 137/625.25 |
| 4,617,012 | 10/1986 | Vaillancourt | 604/29 |
| 4,664,682 | 5/1987 | Monzen | 55/178 |
| 4,770,787 | 9/1988 | Heath et al. | 210/646 |
| 4,822,341 | 4/1989 | Colone | 604/175 |
| 4,846,800 | 7/1989 | Ouriel et al. | 60.4/4 |
| 4,909,780 | 3/1990 | Ouriel et al. | 604/4 |
| 4,988,342 | 1/1991 | Herweck et al. | 604/321 |
| 5,047,011 | 9/1991 | Caron et al. | 604/29 |
| 5,087,250 | 2/1992 | Lichte et al. | 604/321 |
| 5,149,318 | 9/1992 | Lindsay | 604/4 |
| 5,158,533 | 10/1992 | Strauss et al. | 604/4 |
| 5,254,080 | 10/1993 | Lindsay | 604/4 |
| 5,282,783 | 2/1994 | Lindsay | 604/4 |

FOREIGN PATENT DOCUMENTS

| | | |
|---|---|---|
| 0312101 | 4/1989 | European Pat. Off. . |
| 2135890A | 9/1984 | United Kingdom . |
| 91/03217 | 3/1991 | WIPO .................. 604/905 |
| WO91/13640 | 9/1991 | WIPO . |

Primary Examiner—Sam Rimell
Attorney, Agent, or Firm—Gary L. Griswold; Walter N. Kirn; Stephen W. Bauer

[57] ABSTRACT

An apparatus for handling a patient's blood during a first medical use which is convertible for a second medical use comprises a first device, for adapting the reservoir for use during a first medical use and a second device for adapting the reservoir for a second medical use after the first medical use. A lever pivotally mounted on the apparatus, engages at least one of the devices so that pivoting the lever causes the devices to move, moving the first device out of its operative position and moving the second device into its operative position. A lock for the lever locks the devices in place, and a valve mechanism automatically selects a proper outlet.

44 Claims, 5 Drawing Sheets

FIG.10 ered with by the inventor's prior, and U.S. Pat. Nos. 5,149,318

QUICK-CHANGEOVER BLOOD HANDLING APPARATUS

CROSS REFERENCE TO RELATED APPLICATIONS

This is a continuation-in-part application of U.S. patent application Ser. No. 07/898,491, filed Jun. 15, 1992, now abandoned, which is a continuation-in-part application of U.S. patent application Ser. No. 07/493,286, filed Mar. 14, 1990, now U.S. Pat. No. 5,149,318, and U.S. patent application Ser. No. 07/686,495, filed Apr. 7, 1991, now U.S. Pat. No. 5,254,080, which is a continuation-in-part of U.S. patent application Ser. No. 07/493,286, filed Mar. 14, 1990, now U.S. Pat. No. 5,149,318.

BACKGROUND OF THE INVENTION

This invention relates to a quick-changeover blood handling apparatus, and in particular to an apparatus for handling a patient's blood for one medical application which is convertible for use in a second application.

There are instances where one blood handling device would be used for a patient during a medical procedure, and another blood handling or collecting device would be needed for post-procedure care. For example, in the case of heart surgery, a blood reservoir is used as part of the blood recovery and oxygenation system. After the procedure, a separate autotransfusion reservoir might be used to collect the patient's blood from the surgical wound for re-use, and/or another reservoir might simply be used to collect blood drained from the surgical wound for disposal.

Several "convertible" devices are available that can be used both as a blood reservoir during surgery and a pleural drainage unit after surgery. These devices provide several advantages: they eliminate the need for dedicated pleural drainage devices; they minimize the amount of disposable equipment that is used (and must be disposed of); they are more economical; and they reduce staff time associated with setting up multiple devices. Moreover, many of these devices allow for autotransfusion of the collected blood, reducing risk to the patient and reducing the demand for blood products.

However, to varying degrees these devices have also suffered from one significant draw-back: the conversion of these devices from use as a surgical blood reservoir to a drainage unit or to an autotransfusion device is time consuming and complex. Many of these devices come with pages of detailed instructions that the nursing staff is expected to follow to properly disconnect and cap the numerous connectors required for use as a surgical blood reservoir. Some of these devices even require special kits, with further instructions and additional parts that must be set aside and later installed, to make the conversion. This increases the pressure on the nursing staff to quickly and accurately make the conversion. Furthermore, each tube connection that must be undone and capped increases the chance of blood splattering the medical staff, with the attendant risk of spreading disease, such as hepatitis and AIDS.

The inventor's prior, and U.S. Pat. Nos. 5,149,318 and 5,284,080 disclose apparatus for handling a patient's blood during a medical procedure which can be quickly and easily converted for use in blood collection after the procedure. These apparatus eliminate most of the detailed disconnecting and capping steps required by the previously available convertible apparatus by providing an apparatus with a port means and connection blocks that can simply be removed after use in one mode and replaced by new connection blocks specially adapted for use in the new mode. The blocks are mounted in mounting means on the apparatus, and conversion is simply a matter of sliding the proper connection block into its operative position.

As disclosed in U.S. Pat. No. 5,254,080, blocks for different purposes can be separately provided on seal trays. The seal tray seals the block until it is installed on the apparatus. The seal tray can be aligned with the mounting means so that the block can be moved from the seal tray into the mounting means and into alignment with the port means. When the block is no longer needed, it can be returned to its seal tray, which seals the block preventing leakage and contamination. The mounting means preferably comprises a pair of tracks between which the blocks are mounted. The tracks are preferably open at one end to permit installation of blocks from seal trays.

These apparatus can be used during a first medical procedure, and can be quickly and conveniently converted for a second medical procedure. Connections are made to a first block so that the apparatus can be used during the first medical procedure. After the procedure, rather than making numerous disconnections, capping connectors, and closing valves, the first block is moved from its operative position, and may even be removed from the apparatus. A second block, specially adapted for the second procedure is then moved into operative position. All of the parts needed for the conversion are provided on the apparatus, and conversion is simply a matter of changing the blocks.

SUMMARY OF THE INVENTION

The invention provides a further improved quick-changeover blood-handling apparatus which includes a novel means for moving one block out of its operative position and a second block into its operative position. This means for moving the blocks preferably comprises a manually operable lever, pivotally mounted on the apparatus, which engages at least one of the blocks mounted thereon to move the blocks when the lever is pivoted. The lever preferably includes a toothed pinion, and at least one of the devices has a toothed rack adapted to be engaged by the pinion such that rotation of the pinion, caused by the pivoting of the lever, moves the blocks.

Thus, with the apparatus of the present invention a health care worker can convert the apparatus from one use to another simply by manually pivoting the lever, to move a first block (which adapts the apparatus for a first purpose) out of the way, and to move a second block (which adapts the apparatus for a second purpose) into position. The lever provides precise movement of the blocks, so that the blocks are properly positioned. Moreover, the lever provides a mechanical advantage (preferably about four-to-one), making it easier to move the blocks.

Locking means can be provided to lock the lever, and thus the blocks, in position, until they need to be moved, to prevent the blocks from being inadvertently moved.

The lever provides a mechanism for moving the connector blocks without direct contact with the blocks or the tubing connected to them. The lever and its rack-and-pinion linkage with the connector blocks also provides an indication of the position of the connector blocks relative to a port in the apparatus, and the locking means also provides an indexing means for indicating whether a connector block is in proper alignment with the port. Most preferably, the locking means provides an audible and tactile indication when the lever is moved into a position in which one of the connector blocks is aligned with the port.

Most preferably, a valve means is operatively linked with the lever to simultaneously change between two different outlets when the lever is moved between its positions.

These and other advantages will be pointed out hereinafter.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF THE PREFERRED EMBODIMENT

Figure 1:
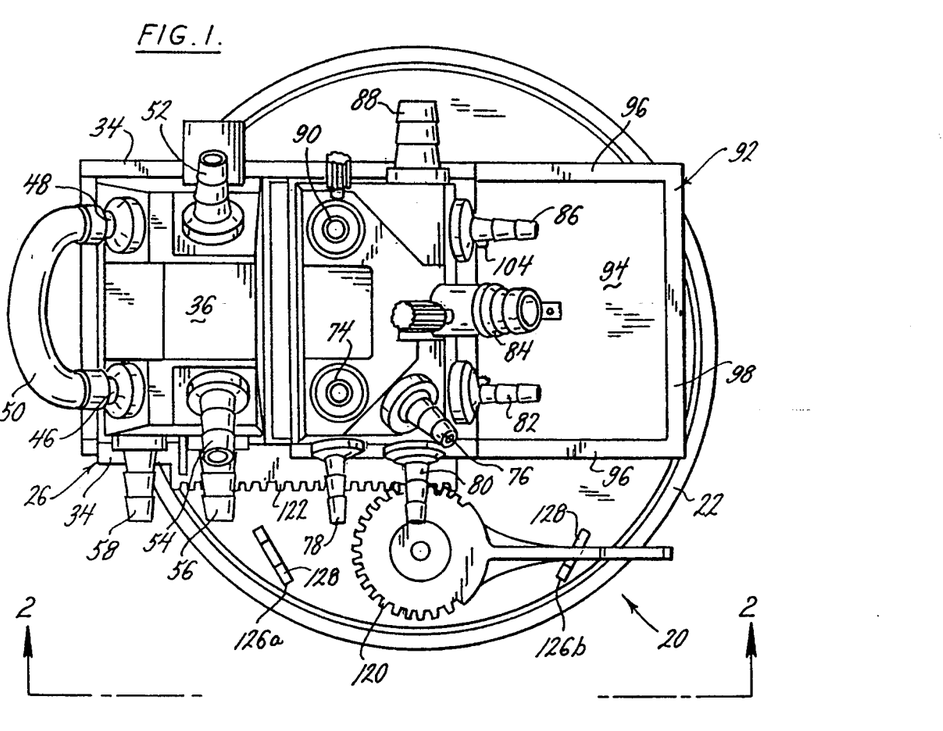
FIG. 1 is a top plan view of a blood handling apparatus constructed according to the principles of this invention.

A surgical blood handling apparatus constructed according to the principles of this invention is indicated generally as 20 in FIG. 1. The surgical blood apparatus 20 can be adapted for use as part of a blood recovery and oxygenation system of the type used during cardiac surgery, and for post surgery in blood collection. Although described with respect to surgical blood apparatus 20, this invention is not so limited, and could be applied to other blood-handling apparatus convertible among two or more medical uses. The apparatus 20 described can be conveniently and inexpensively made from plastic, so that it can be disposed of when its several uses are over.

The surgical blood apparatus 20 comprises a lid 22 mounted on a reservoir 24. The lid 22 and reservoir are preferably constructed to permit the lid 22 to rotate with respect to reservoir 24, while maintaining a seal.

The reservoir 22 and its function are described in more detail in prior and U.S. Pat. Nos. 5,149,318, and 5,254,080 both of which are incorporated herein by reference.

A first block, for example ICU block 26, is slidably mounted on the lid 22 to adapt the reservoir 24 for a particular function or use, in the case of block 26, for use as a blood collection device in an intensive care unit. One or more other blocks, for example OR block 28 can be releasably installed on the lid 22 to selectively adapt the reservoir 24 for one or more other uses, in the case of OR block 28, for use in a blood oxygenation circuit during heart surgery.

The lid 22 comprises at least one port means 30 comprising at least one opening 32 communicating with the reservoir 22. A pair of generally parallel tracks 34 is provided on the lid 22 to slidably mount at least one block thereon. This block may be a block to simply occlude the port means 30, or as in this preferred embodiment, it may be an ICU block 26. The tracks 34 preferably have an inverted "L" shape configuration with a laterally extending flange for engaging a portion of the blocks and holding them on the lid 22 while permitting the blocks to slide. At least one end of the tracks 34 is preferably open to permit removing the blocks from the tracks 34 and reservoir 24, and mounting the blocks on the track 34.

The ICU block 26 comprises a hollow dome-like shell 36. A plurality of internal walls (not shown) divide the interior of the shell 36 into a plurality of compartments. There are preferably three walls that divide the shell 36 into four compartments. The shell 36 is mounted on a base 38, which isolates the compartments from each other. The underside of the base 38 has at least one recessed generally annular groove 40 therein for receiving a sealing gasket 42 so that when the base 38 is properly aligned with the port means 30, a seal is formed between the lid 22 and base 38 encompassing the openings 32 comprising the port means 30. In the preferred embodiment the sealing gaskets 42 are endless loops.

There are openings 44 in the base 36 inside at least some of the gaskets, that allow sealed communication between the reservoir 24 and at least some of the compartments in the ICU block 26. In the preferred embodiment there are three openings in the base 36 of the ICU block 26, which allow communication between openings 32 and the various compartments in the ICU block 26 so that the ICU block 26 effectively seals the openings 32.

The ICU block 26 has a plurality of connectors for making connections, via the various internal compartments, with the reservoir 24. A first connector 46 to one of the compartments and a second connector 48 to another of the compartments are connected by a piece of preferably transparent tubing 50 to allow pressure equalization between various portions of the reservoir 24. If a portion of the reservoir 24 becomes plugged, blood will be drawn through the transparent tubing 50, providing a visual indication of the blockage. The ICU block 26 may also be provided a mushroom-type pressure relief valve (not shown), well known in the art, that relieves excess pressure differential when the pressure differential between the interior and the exterior of the reservoir 24 is greater than predetermined maximums. The valve is configured to allow gas to escape when the pressure inside the reservoir 24 exceeds the ambient pressure by more than a predetermined maximum. The valve is also configured to allow ambient gas to enter the reservoir 24 when the ambient pressure exceeds the pressure in the reservoir 24 by more than a predetermined maximum. There is also a third connector 52, which can be used to connect a vacuum line to the reservoir 24. Finally, there are fourth, fifth, and sixth connectors 54, 56, and 58, which can be used to connect chest drainage tubes to the reservoir 24.

The forward end of the base 36 has an upstanding lip 60 to engage other blocks, as described below.

The lid 22 is constructed and adapted so that other blocks can be selectively mounted thereon, in alignment with the port means 30, to adapt the reservoir 24 for various functions. As shown in this preferred embodiment, one such possible block is OR block 28. The OR block 28 is generally similar in construction to block 26. The OR block 28 comprises a hollow dome-like shell 62. A plurality of internal walls divide the interior of the shell 62 into a plurality of compartments. In the preferred embodiment there are two walls that divide the shell 62 into three compartments. The shell 62 is mounted on a base 64, which isolates the compartments from each other. The underside of the base 64 has at least one recessed, generally annular groove therein, like groove 40 in the base 34. The groove in the underside of the base 64 receives a sealing gasket, like sealing gasket 42, so that when the base 64 is properly aligned with the port means 30, a seal is formed between the lid 22 and base 64 encompassing the openings 32 comprising the port means 30. In this preferred embodiment there are four grooves each holding an endless loop sealing gasket that seals one of the four openings comprising the port means 30.

There are openings in the base 64 inside at least some of the gaskets, like the openings 44 in base 34, that allow sealed communication between the reservoir 24 and at least some of the compartments in the block 28. In the preferred embodiment there are three openings in the base 64 of the OR block 28, which allow communication between the openings 32 and the compartments. There is no opening inside one of the gaskets and thus the OR block 28 effectively seals one of the openings.

The OR block 28 comprises a plurality of connectors for making connections, via the various internal compartments, with the reservoir 24. There is a connector 74 for adding prime solution directly into the filtered area of reservoir 24. There are connectors 76, 78, 80, and 82 for attachment to blood suction lines from the surgical site. There is a connector 84 for attaching a venous return blood line from the patient. There is a connector 86 for optionally attaching a drain tube from a cardiotomy device. There is a connector 88 for attachment of a blood and/or prime tube from the outlet side of the blood oxygenator (typically the recirculation port). There is one connector 90 that allows both the priming of the reservoir 24 outside the filter and venting the reservoir 24.

Figure 3:
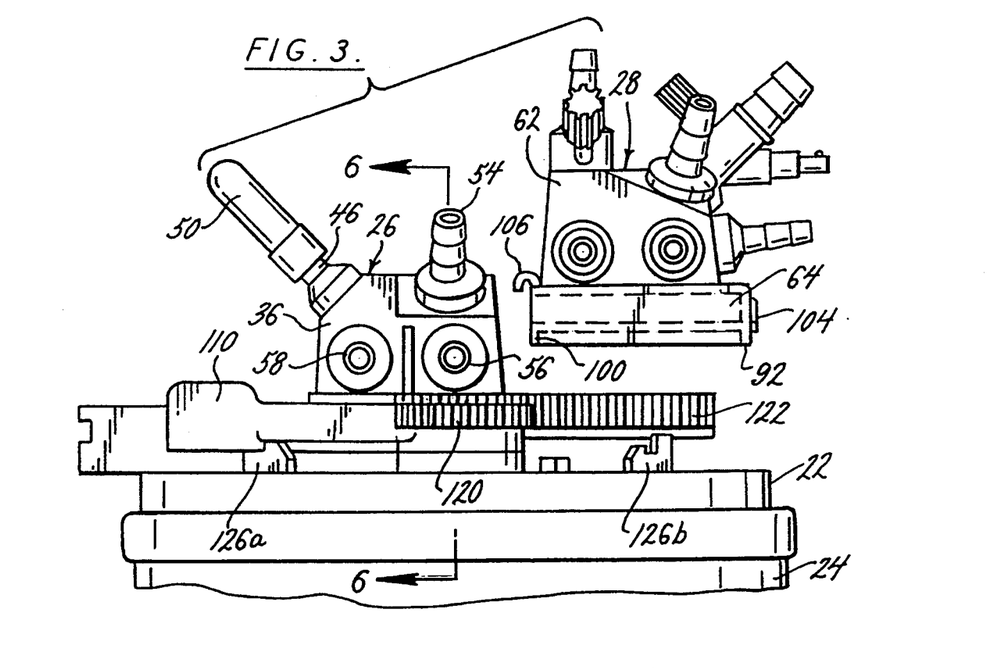
FIG. 3 is a side elevation view of the blood handling apparatus showing a block being installed thereon.

The OR block 28 is slidably mounted on a seal tray 92. Of course, other types of blocks can be provided on seal trays 92, to adapt the apparatus to other medical uses than as a blood handling device for heart surgery. The seal tray 92 has a bottom surface 94 for sealingly engaging the gaskets on the base of the block 28. The seal tray 92 preferably has raised side rails 96, alignable with the tracks 34 on the lid 22, and a raised back 98 to retain the block on the seal tray 92. There is a depending lip 100 around the seal tray 92, the front portion of which is adapted to fit over a raised boss or land 102 on the lid 22 when the seal tray 92 is aligned with the tracks 34. The lip 100 and the land 102 cooperate to retain the seal tray 92 in position aligned with the tracks 34 against side-to-side movement or movement away from the tracks 34. There may be notches 103 in the land 102 for engaging bosses on the seal tray 92 to further ensure proper registration between the seal tray 92 and the tracks 34. The base 64 of the block 28 has feet 104 adapted to engage the seal tray 92 when the block 28 is in the tracks 34. The feet 104 hold the seal tray 92 down against vertical movement, and cooperate with the lip 100 and land 102 to retain the seal tray 92 in alignment with the tracks 34 while the block 28 is in the tracks 34. The raised back 98 has openings (see FIG. 3) through which the feet 104 project when the block 28 is mounted in the seal tray 92.

The forward edge of the base 64 of the block 28 has an inverted channel 106 adapted to engage the raised lip 60 on the base 34 of the block 26 so that the two blocks 26 and 28 move together in the tracks 34.

Means is provided for moving the blocks in the tracks 34, so that the block currently in alignment with the port means 30 can be moved out of alignment with the port means 30, and another block can be moved into alignment with the port means 30. In this preferred embodiment, the moving means comprises a lever 110, pivotally mounted on the lid 22. The lever 110 is pivotally mounted on a retainer 112 secured on the lid 22 with bolt 114. The retainer 112 has a generally T-shaped vertical cross-section (see FIG. 6) with a vertically extending shaft 116 on which the lever is mounted 110, and a radially projecting flange 118 that engages the lever 110 and retains it on the lid 22. The retainer 112 could alternatively be formed integrally with the lid 22, and be resiliently compressible so that the lever 110 can be snapped onto the retainer 112.

The lever 110 engages at least one of the blocks in the tracks 34 to move the block when the lever 110 is pivoted. The lever 110 preferably includes a toothed pinion 120 adapted for non-slipping engagement with a toothed rack 122 on at least one of the blocks. Preferably, the pinion 120 and lever 110 are integrally molded of suitable plastic material, such as polycarbonate.

Figures 6, 7:
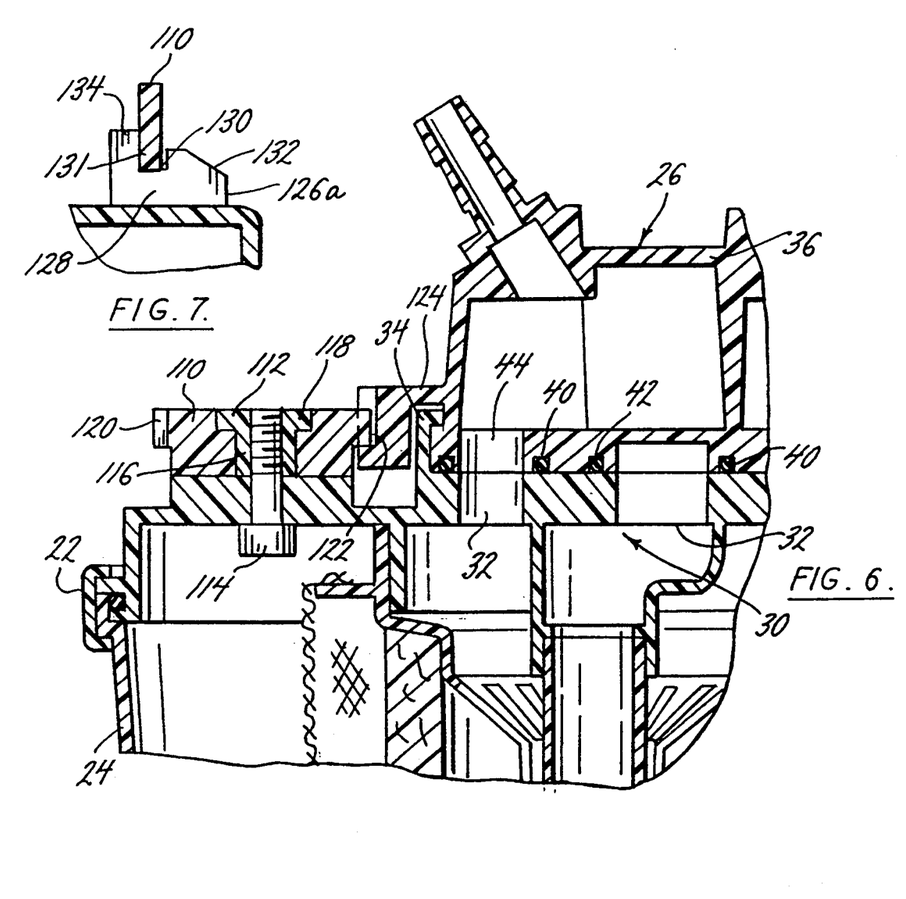
FIG. 6 is a partial vertical cross-sectional view of the blood handling apparatus, taken along the plane of line 6—6 in FIG. 3.
FIG. 7 is a partial vertical cross-sectional view of the blood handling apparatus, taken along the plane of line 7—7 in FIG. 4.

In the preferred embodiment, the rack 122 is mounted on the ICU block 26, which is the block initially provided in the tracks 34. As shown in FIG. 6, a flange 124 extends laterally from the side of the ICU block 26, above the top of the track 34. The rack 122 depends downwardly from the end of the flange 124, on the opposite side of the track 34 from the ICU block 26, so that it can be freely engaged by the pinion 120. The rack 122 preferably extends beyond the front of the block 26 so that when a second block, for example, block 28, is attached to lip 60, the rack 22 also extends along the side of the second block 28. This allows the lever 110 to be conveniently sized and positioned on the lid 22. It further allows blocks to be easily installed and removed from the lid 22. Alternatively, racks could be placed on all the blocks, or the pinion 120 could be resized or repositioned to engage a rack that is the same size as the side of the first block.

As the pinion 120 rotates as the lever 110 is pivoted, the teeth of the pinion 120 engage the teeth of the rack 122, and advance the ICU block 26. Thus, the lever 110 can be pivoted to move the ICU block 26 (and OR block 28 connected to the ICU block 26) in either direction in the track 34.

The non-slipping engagement between the teeth of the pinion 120 and rack 122 allows the lever 110 to provide an indexing function. That is, the rotational position of the lever 110 provides an indication of the position of the ICU block 26 along the track 34. For example, the position of the lever 110 provides an indication of whether the ICU block 26 or OR block 28 is in alignment with the port means 30.

Figure 2:
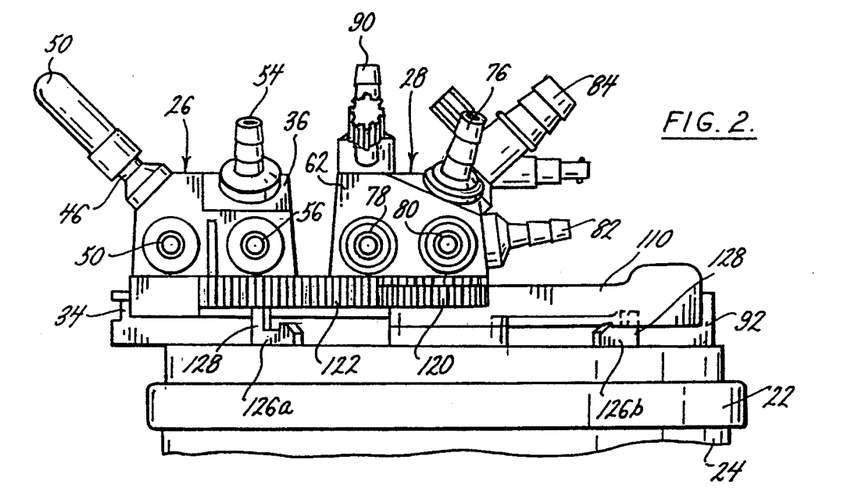
FIG. 2 is a side elevation view of the blood handling apparatus, taken along line 2—2 in FIG. 1.

At least one means for releasable locking the lever 110 is provided to secure the blocks in position in the tracks 34. In the preferred embodiment there are two such locking means 126a and 126b, one of which (126a) engages the lever 110 when the ICU block 26 is its forward-most position in track 34 (see FIGS. 4 and 5), in alignment with the port means 30, and the other of which (126b) engages the lever 110 when the ICU block 26 is in its rearward-most position in track 34 (see FIGS. 1 and 2), and the OR block 28 is in alignment with the port means 30. Each of the locking means 126 comprises a tab 128, projecting upwardly from the top surface of the lid 22. As best shown in FIG. 7, the tab 128 has a recess 130 in its top edge for receiving a rib 131 depending from the bottom of the lever 110. The front portion 132 of the top edge of the tab 128 has a sloped configuration to cam the lever 110 and its depending rib 131 upwardly to pass over the tab 128 to the recess 130. The lever 110 and rib 131 flex slightly upwardly, and resiliently snap back as the rib 131 aligns with the recess 130, providing and audible and tactile confirmation that the lever 110 is locked. The back portion of the tab 128 has a vertical projection 134 that extends sufficiently to engage the side of the lever 110, to prevent overpivoting of the lever 110.

The lever 110 is quickly and readily released, by simply flexing the lever 110 upwardly sufficiently to clear the recess 130, and rotating the lever 110 in the direction over the front/sloped portion 132 of the tab. The edges of the tab 128 forming the recess 130 can be provided with a suitably steep slope which helps flex the lever 110 upwardly out of the recess 130 when the lever 110 is manually pivoted while being sufficiently steep to secure the lever 110 in position against inadvertent movement.

The lever 110 provides a mechanical advantage (e.g., four-to-one), facilitating moving of blocks in the tracks 34. The lever 110 allows the blocks to be moved without requiring direct contact with the blocks, reducing the risk of disturbing the tubing connections to the blocks. The locking devices 126a and 126b limit the travel of the lever 110, and thus the blocks, and provide a positive indication when the blocks are properly positioned. The locking means 126a and 126b further resists unintended movement of the blocks from their operative positions.

The respective recesses 130 of the first and second locking means 126a and 126b define the lever's first and second positions, respectively. In the first position (FIGS. 3 and 4), the lever 110 is held in position by the first locking means 126a to maintain the ICU block 26 in alignment with the port means 30. In the second position (FIGS. 1 and 2), the lever 110 is held in position by the second locking means 126b to maintain the OR block 28 in alignment with the port means 30. The recesses 130 of the first and second means 126a and 126b releasably receive a portion of the lever 110 (e.g., the depending rib 131) to releasably hold the lever 110 in its first and second positions, respectively.

In an alternative embodiment, both the ICU and OR blocks could be initially provided on the track (as shown in FIG. 1), and the lever can be operated to move one device out of its operative position in the track, either out of the way or out of the tracks entirely.

Figure 8:
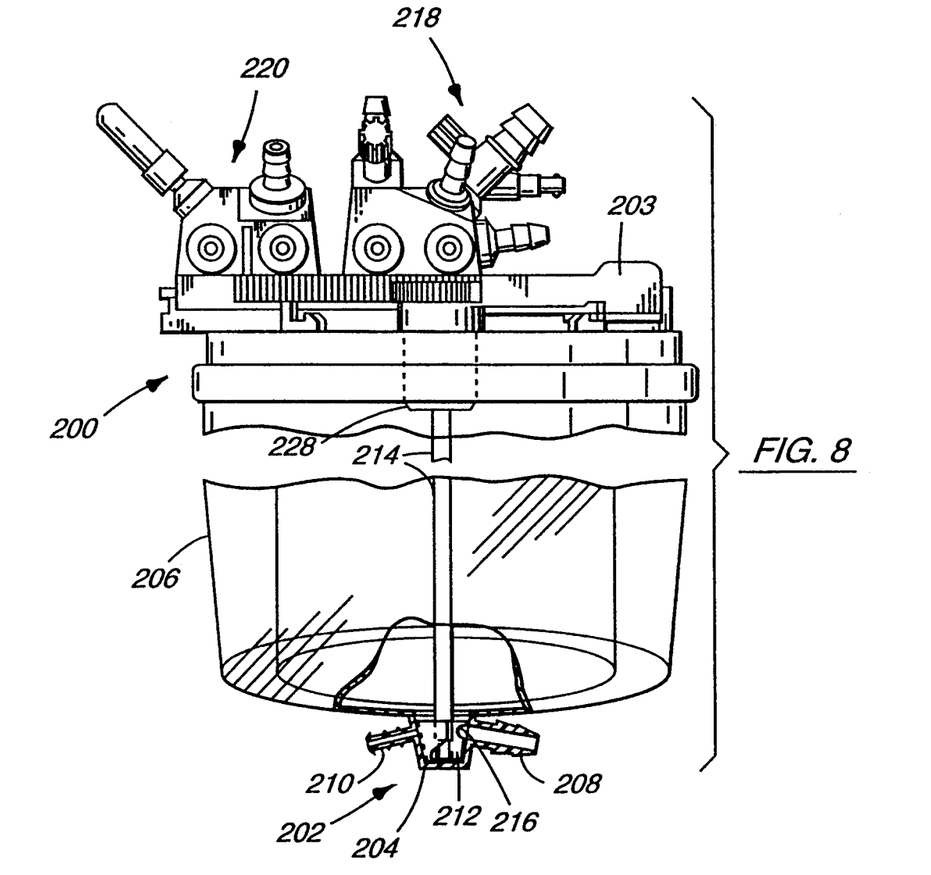
FIG. 8 is a side elevation view, partially broken away, of another embodiment of the blood handling apparatus, illustrating a drainage valve mechanism as part of the apparatus.
Figure 9:
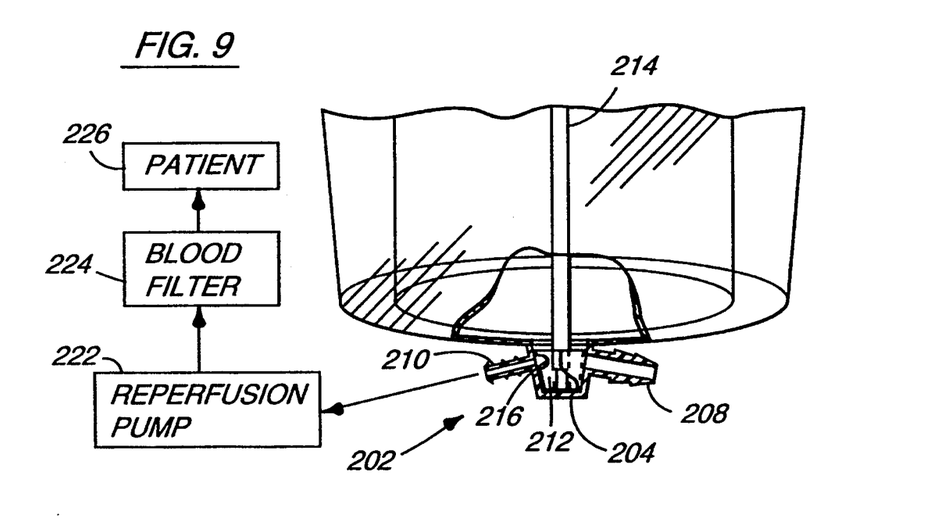
FIG. 9 is a side elevation view of a portion of the apparatus of FIG. 8, illustrating a second position of the drainage valve mechanism of FIG. 8.
Figure 10:
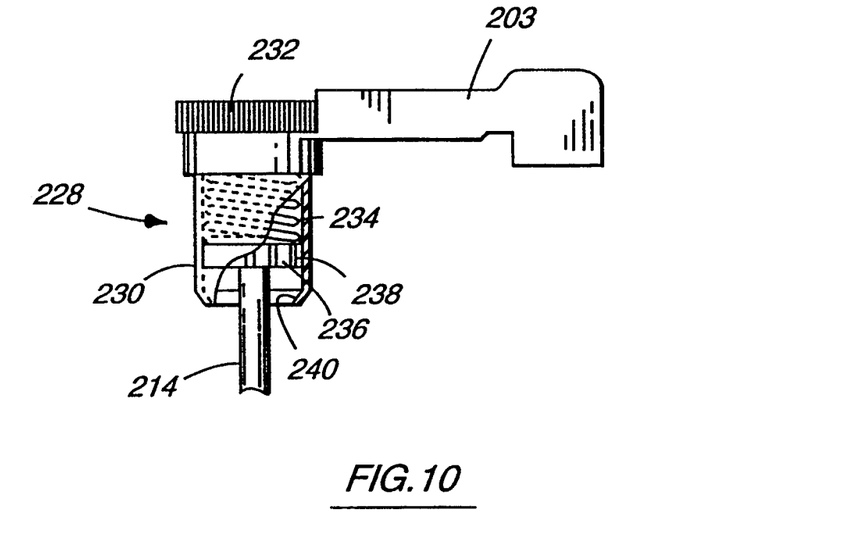
FIG. 10 is an enlarged elevational view of a spring-loaded mechanism, also shown in FIG. 8 at reference numeral 228, for biasing a valve member in the drainage valve mechanism.

FIGS. 8-10 illustrate another embodiment of the apparatus of the invention which is identical to the apparatus of FIGS. 1-7 except that the apparatus 200 of FIGS. 8-10 includes a reservoir drain conversion feature, and, in the example of FIGS. 8-10, the lid of the reservoir 206 is not rotatable. This feature is provided by a drainage valve mechanism 202 operatively linked with a lever 203 and pinion 232 otherwise identical to the lever 110 and pinion 120 of FIGS. 1-7.

The drainage valve mechanism 202 comprises a valve housing 204 at the bottom of reservoir 206, two outlets 208 and 210 on the valve housing 204, and a valve body 212 rotatable within the valve housing 204 to direct blood exiting the apparatus 200 to one or the other of the outlets 208 or 210. One end of a valve control shaft 214 is connected to the valve body 212 and the other end of the valve control shaft 214 is attached to the lever 203 such that the valve control shaft 214 and valve body 212 are rotated when the lever 203 is turned. The valve control shaft 214 is co-axial with the axis of rotation of the lever 203 and the valve body 212.

Preferably, the valve body 212 comprises a generally frustoconical cup-shaped member 212 having a single opening 216 through the side wall of the cup-shaped member 212. The cup-shaped member 212 is open along its top to allow entry of blood from the reservoir into the cup-shaped member 212.

The opening 216 in the cup-shaped member 212 is movable between an OR position (FIG. 8), in which the opening 216 is aligned with outlet 208, and an ICU position (FIG. 9), in which the opening 216 is aligned with outlet 210. The opening 216 is in the OR position (FIG. 8) when the lever 203 holds the OR block 218 in alignment with the port means (identical to port means 30). The opening 216 is in the ICU position (FIG. 9) when the lever 203 holds the ICU block 220 in alignment with the port means. The means 126a and 126b for releasably locking the lever described with respect to the apparatus of FIGS. 1-7 also functions to hold the opening 216 in position relative to the outlets 208 and 210.

When the opening 216 is in its OR position (FIG. 8), the outlet 208 allows drainage of fluid from the reservoir 206 into tubing (not shown) connected to the outlet 208. That tubing would be connected to a blood pump (not shown) to pump drained blood into a blood oxygenator. The blood pump and blood oxygenator may be of conventional design used in extracorporeal cardiovascular support systems. After the patient's heart is taken off bypass, the tubing may be clamped generally adjacent the outlet 208 and the tubing cut downstream of the clamp (not shown).

After the opening 216 is moved to its ICU position (FIG. 9), the outlet 210 allows drainage through tubing into a conventional reperfusion pump 222, which pumps the drained blood through a conventional blood filter 224 back to the patient 226. The outlet 210 may include a conventional luer connector. As discussed above with respect to the apparatus of FIGS. 1-7, when the ICU block 220 is moved into alignment with the port means, the OR block 218 is moved onto the seal tray so that the seal tray and OR block 218 may be removed from the apparatus 200.

When the opening 216 is between the outlets 208 and 210, both outlets 208 and 210 are closed.

Preferably, the side walls of the cup-shaped member 212 define an included angle of approximately 30-60 degrees, and the cavity of the valve housing 204 receiving the cup-shaped member 212 has complementary taper such that the cup-shaped member 212 functions as a stopper to prevent leakage. Most preferably, one of the valve housing 204 and the cup-shaped member 212 is formed of a relatively soft material, and the other of the valve housing 204 and the cup-shaped member 212 is formed of a relatively hard material. In addition, a spring-loaded mechanism 228 (FIG. 10) is preferably provided to load the cup-shaped member 212 downwardly into the cavity of the housing 204.

The spring-loaded mechanism 228 preferably comprises a socket 230 extending downwardly into the reservoir 206 from the pinion 232 for receiving the top end of the shaft 214, and a coil spring 234 pushing the shaft 214 downwardly and thus the cup-shaped member 212 into the cavity of the valve housing 204. The top end 236 of the shaft 214 is preferably enlarged relative to the rest of the shaft 214, and is provided with a plurality of splines 238 intermeshing with grooves (not shown) in the socket 230 to ensure that the shaft 214 rotates with the pinion 232 and lever 203. The bottom 240 of the socket 230 may have a cross section smaller than the enlarged top end 236 of the shaft 214, and have sufficient resilience to permit the top end 236 to be inserted into the socket 230.

It will be appreciated that one advantage of the reservoir drain conversion feature of FIGS. 8-10 is to automatically convert the reservoir outlet for a different use when the reservoir inlets are converted by moving the OR and ICU blocks.

OPERATION

The operation of the invention will be further described with reference to the apparatus of FIGS. 1-7.

Figure 4:
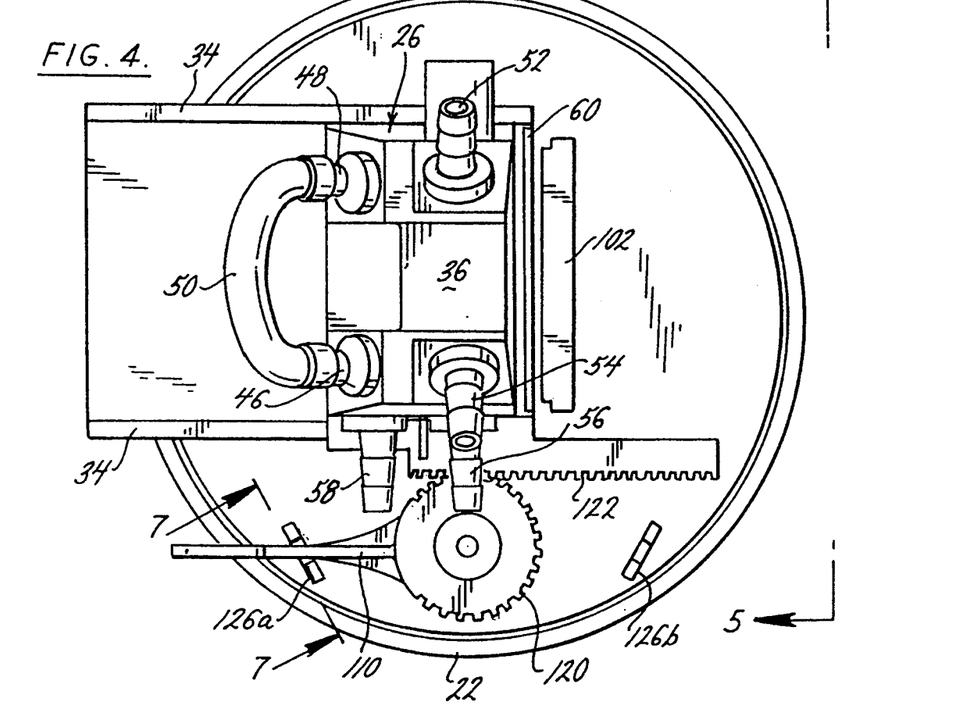
FIG. 4 is a top plan view of the blood handling apparatus before a second block is installed thereon.
Figure 5:
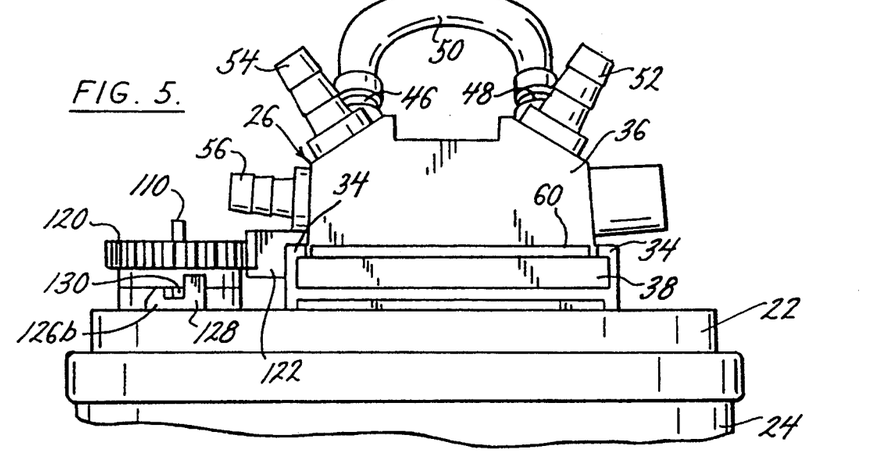
FIG. 5 is a side elevation view of the blood handling apparatus, taken along line 5—5 in FIG. 4.

The lid 22 is adapted to receive different functional blocks to adapt the apparatus 20 to different medical functions. As described in the preferred embodiment, the apparatus 20 is initially set up for use in an intensive care unit, with an ICU block 26 mounted in the tracks 34 on the lid 22, in alignment with the port means 30, all as shown in FIG. 4. (Of course, some other block could be provided, for example, a simple cover block to close and seal the port means 30.) If it were desired to adapt the reservoir 24 for use in surgery, an OR block 28, on a seal tray 92, would be aligned with the tracks 34, as shown generally in FIG. 5.

The depending lip 100 on the seal tray 92 would be fit over the land 102 on the lid 22, helping to align the seal tray 92 with the tracks 34, and to hold the seal tray 92 in place. As the seal tray 92 is put into place, the inverted channel 106 on the base 64 of the block 28 fits over the raised lip 60 on the base 34 of the block 26, releasably securing the blocks 26 and 28 together so that they will slide in unison in the tracks 34.

The lever 110 would then be lifted to bring the rib 131 out of engagement with recess 130, and the lever 110 would be pivoted. As the lever 110 pivots, the pinion 120 rotates, moving the rack 122, and thus moving the ICU block 26 rearwardly in the tracks 34, out of alignment with the port means 30. Because the ICU and OR blocks 26 and 28 are interlocked, this simultaneously draws the OR block 28 off of the seal tray 92, and into the tracks 34, until the OR block 28 aligns with the port means 30. As the OR block 28 comes into alignment with the port means 30, the lever 110 is cammed up by the front edge 132 of the tab 128, the lever 110 passes over the top of the tab 128 until the rib 131 snaps into the recess 130, releasably locking the lever 110 in position with the OR block 28 in alignment with the port means 30. The feet 104 projecting from the base 64 of the block 28 hold the seal tray 92 in place on the lid 22.

Connections can now be made with the various connectors on the OR block 28. Alternatively, the OR block 28 can be pre-connected with the various devices used during surgery, and quickly installed on the reservoir 24 when needed. For example, the OR block 28, connected tubing, and seal tray 92 could be provided as a pre-packaged set, and the OR block 28 and seal tray 92 simply dropped onto the lid 22, and the lever 110 pivoted to prepare the apparatus 20 for surgery.

When the procedure is over, the lever 110 is lifted until the rib 131 clears the recess 130, and the lever 110 is pivoted. As the lever 110 pivots, the pinion 120 rotates, moving the rack 122, and thus moving the block 26 forwardly in the track 34, back into alignment with the port means 30. Because the ICU and OR blocks 26 and 28 are interlocked, this simultaneously pushes the OR block 28 out of the tracks 34, back onto the seal tray 92. As the ICU block 26 comes back into alignment with the port means 30, the lever 110 is cammed up by the front edge 132 of the tab 128. The lever 110 passes over the top of the tab 128 until the rib 131 snaps into the recess 130, releasably locking the lever 110 in position with the ICU block 26 aligned with the port means 30. The OR block 28 can simply be removed from the reservoir 24, with the seal tray 92, closing the ports in the bottom of the OR block 28, thereby avoiding spills and contact with the patient's bodily fluids. The OR block 28 can be discarded with the tubing connections intact, to prevent leakage.

The seal tray 92 seals the openings in the base 64, thereby reducing the risk of spillage and contamination. The ICU block 26 is again locked in position over the port means 30, and the lid 22 is ready to receive another block on a seal-tray 92 to adapt the reservoir 22 to a further use. The seal tray 92 also acts as a seal against spillage and contamination prior to surgery, for example during construction of the block, attachment of the tubing, and during sterilization and storage.

The apparatus 20 or 200 would most preferably be supplied with the ICU block 26 or 220 mounted on the track 34, and the OR block 28 or 218 already connected with its appropriate tubing set (not shown). After unpackaging the apparatus 20 or 200 and the tubing set (with the OR block), the normal practice would be to align the seal tray 92 and move the OR block 28 or 218 into operative position. This would also move the ICU block 26 or 220 out of alignment with the port 30. After surgery, the OR block 28 or 218 would be removed from the track 34 onto the seal tray 92, and the seal tray 92, OR block 28 or 218, and much of the associated tubing discarded. The ICU block 26 or 220 would then be used after surgery in order to supply scavenged blood from the surgical site to the reservoir 24 or 206.

As various changes could be made in the above constructions without departing from the scope of the invention, it is intended that all matter contained in the above description or shown in the accompanying drawings shall be interpreted as illustrative and not in a limiting sense.

I claim:

1. An apparatus for handling a patient's blood during medical procedures which is convertible for multiple medical uses, the apparatus comprising:
- a reservoir;
- a port in the reservoir comprising at least one opening;
- a first block alignable with the port for adapting the reservoir for a first medical use, the first block including first connection means for connecting tubing to the first block in fluid communication with the port when the first block is aligned with the port;
- a second block, separate from the first block, alignable with the port, for adapting the reservoir for a second medical use, the second block including second connection means for connecting tubing to the second block in fluid communication with the port when the second block is aligned with the port;
- means for mounting the first and second blocks on the reservoir with the first block initially aligned with the port to allow the reservoir to be used for the first medical use, the mounting means allowing the first block to be moved out of alignment with the port and the second block to be moved into alignment with the port to allow the reservoir to be used for the second medical use; and
- rack-and-pinion lever means for moving the first block out of alignment with the port and for moving the second block into alignment with the port.

2. The apparatus according to claim 1 wherein the rack-and-pinion lever means for moving the first and second blocks comprises a lever, pivotally mounted on the reservoir, which engages at least one of the first and second blocks to move both of the blocks when the lever is pivoted.

3. The apparatus according to claim 2 wherein the lever includes a toothed pinion, and wherein at least one of the blocks has a toothed rack adapted to be engaged by the pinion such that rotation of the pinion caused by the pivoting of the lever, moves the blocks.

4. The apparatus according to claim 2 further comprising:
- first and second outlets mounted on the reservoir; and
- valve means, operatively linked with the lever, for allowing drainage through the first outlet but not the second outlet when the lever moves the first block into alignment with the port and allowing drainage through the second outlet but not the first outlet when the lever moves the second block into alignment with the port.

5. The apparatus according to claim 4 wherein the valve means comprises a generally cup-shaped member having a wall with an opening formed therethrough, and a shaft connecting the cup-shaped member to the lever such that pivoting the lever rotates the cup-shaped member to bring the opening of the cup-shaped member into alignment with one or the other of the first and second outlets.

6. The apparatus according to claim 1 wherein the means for mounting the first and second blocks comprises a pair of generally parallel tracks between which the first and second blocks are slidably mounted.

7. The apparatus according to claim 1 wherein the first and second blocks are releasably connected together so that they move together.

8. An apparatus for handling a patient's blood during medical procedures which is convertible for multiple medical uses, the apparatus comprising:
- a reservoir;
- a port in the reservoir comprising at least one opening;
- a first block alignable with the port for adapting the reservoir for a first medical use., the first block including first connection means for connecting tubing to the first block in fluid communication with the port when the first block is aligned with the port;
- a second block, separate from the first block, alignable with the port, for adapting the reservoir for a second medical use, the second block including second connection means for connecting tubing to the second block in fluid communication with the port when the second block is aligned with the port;
- mounting means for movably mounting the first and second blocks on the reservoir so that the first block can be aligned with the port to allow the reservoir to be used for the first medical use, and so that the first block can be moved out of alignment with the port and the second block to be moved into alignment with the port to allow the reservoir to be used before or after the first medical use for a second medical use; and
- a lever pivotally mounted on the reservoir and having a pinion that engages at least one of the first and second blocks to move the first and second blocks when the pinion rotates as the lever is pivoted.

9. The apparatus according to claim 8 wherein the pinion comprises a toothed pinion, and wherein at least one of the first and second blocks has a toothed rack adapted to be engaged by the pinion such that rotation of the pinion caused by the pivoting of the lever, moves the first and second blocks.

10. An apparatus for handling a patient's blood during medical procedures which is convertible for multiple medical uses, the apparatus comprising:
- a reservoir;
- a port in the reservoir comprising at least one opening;
- a first block alignable with the port for adapting the reservoir for a first medical use, the first block including first connection means for connecting tubing to the first block in fluid communication with the port when the first block is aligned with the port;
- a second block, separate from the first block, alignable with the port, for adapting the reservoir for a second medical use, the second block including second connection means for connecting tubing to the second block in fluid communication with the port when the second block is aligned with the port;
- mounting means for movably mounting the first and second blocks on the reservoir so that the first block can be aligned with the port to allow the reservoir to be used for the first medical use, and so that the first block can be moved out of alignment with the port and the second block to be moved into alignment with the port to allow the reservoir to be used before or after the first medical use for a second medical use;
- a lever, pivotally mounted on the reservoir, which engages at least one of the first and second blocks to move the first and second blocks when the lever is pivoted;

first and second outlets mounted on the reservoir; and valve means, operatively linked with the lever, for allowing drainage through the first outlet but not the second outlet when the lever moves the first block into alignment with the port and allowing drainage through the second outlet but not the first outlet when the lever moves the second block into alignment with the port.

11. The apparatus according to claim 10 wherein the valve means comprises a generally cup-shaped member having a wall with an opening formed therethrough, and a shaft connecting the cup-shaped member to the lever such that pivoting the lever rotates the cup-shaped member to bring the opening of the cup-shaped member into alignment with one or the other of the first and second outlets.

12. An apparatus for handling a patient's blood during medical procedures which is convertible for multiple medical uses, the apparatus comprising:

a reservoir;

a port in the reservoir comprising at least one opening;

a first block alignable with the port for adapting the reservoir for a first medical use, the first block including first connection means for connecting tubing to the first block in fluid communication with the port when the first block is aligned with the port;

a second block, separate from the first block, alignable with the port, for adapting the reservoir for a second medical use, the second block including second connection means for connecting tubing to the second block in fluid communication with the port when the second block is aligned with the port;

a track for slidably mounting the first and second blocks on the reservoir, so that the first block can be aligned with the port to allow the reservoir to be used for the first medical use, and so that the first block can be moved out of alignment with the port and the second block to be moved into alignment with the port to allow the reservoir to be used before or after the first medical use for a second medical use; and a lever pivotally mounted on the reservoir and having a pinion that engages at least one of the first and second blocks to move the first and second blocks along the track when the pinion rotates as the lever is pivoted.

13. The apparatus according to claim 12 further comprising a rack mounted on one of the first and second blocks, the pinion being mounted on the lever in non-slipping engagement with the rack such that pivoting the lever also pivots the pinion to move the rack, thereby moving the first and second blocks along the track, the lever being mounted for pivotable movement between a first position, wherein the first block is held in alignment with the port, and a second position, in which the second block is held in alignment with the port.

14. The apparatus according to claim 13 wherein the rack is mounted on the first block, the second block being releasably attachable to the first block so that, as the lever is pivoted to move the first block, the second block is also moved.

15. The apparatus according to claim 13 further comprising means for releasably locking the lever in the first and second positions to secure either the first block or the second block in alignment with the port.

16. The apparatus according to claim 15 further comprising:

first and second outlets mounted on the reservoir; and valve means, operatively linked with the lever, for allowing drainage through the first outlet but not the second outlet when the lever is in its first position and allowing drainage through the second outlet but not the first outlet when the lever is in its second position.

17. The apparatus according to claim 16 wherein the valve means comprises a generally cup-shaped member having a wall with an opening formed therethrough, and a shaft connecting the cup-shaped member to the lever such that pivoting the lever rotates the cup-shaped member to bring the opening of the cup-shaped member into alignment with the first outlet when the lever is in its first position and to bring the opening of the cup-shaped member into alignment with the second outlet when the lever is in its second position.

18. The apparatus according to claim 15 wherein the means for releasably locking the lever comprises first and second means, each having a recess, for releasably receiving a portion of the lever to releasably hold the lever in its first and second positions, respectively.

19. The apparatus according to claim 18 wherein the first and second means includes means for preventing overpivoting of the lever beyond the first and second positions.

20. The apparatus according to claim 18 wherein the first and second means comprises first and second tabs extending from the reservoir and defining the lever-receiving recesses, each of the first and second tabs having a sloped front portion on one side of the recess to cam the lever over the tab and into the recess, and a projection on the other side of the recess to prevent overpivoting of the lever beyond the recess.

21. The apparatus according to claim 18 further comprising means for providing an audible and tactile indication when the lever is locked into either of its first and second positions.

22. A connection system for facilitating connections with a blood handling apparatus, to adapt the blood handling apparatus for particular medical use, the system comprising:

a lid for the blood handling apparatus, the lid having at least one port which comprises at least one opening communicating with the blood handling apparatus;

a track for movably mounting one or more blocks on the lid, so that the blocks on the lid can be aligned with the port and moved out of alignment with the port;

at least one connector block, each connector block having at least one access opening for communicating with the port in the base, and at least one connection device for making a connection to the connector block to adapt the blood handling apparatus for a particular medical use when the connector block is in communication with the blood handling apparatus;

a seal tray for movably mounting each connector block and initially sealing the connector block's access openings, the seal tray and the base being configured so that the seal tray can be aligned with the track to allow the connector block to be moved at least partially off of the seal tray and in the track, to bring the connector block's access openings into alignment with the port; and rack-and-pinion lever means for moving the connector block from the seal tray aligned with the track, at least partially off of the seal tray and into the track to bring the connector block's access openings into alignment with the port.

23. The system according to claim 22 wherein the rack-and-pinion lever means for moving the connector block comprises a lever, pivotally mounted on the lid, which moves the connector block when the lever is pivoted.

24. The system according to claim 23 wherein the lever includes a toothed pinion, and wherein the connector block is connected to a toothed rack adapted to be engaged by the pinion such that rotation of the pinion caused by the pivoting of the lever, moves the connector block.

25. The system according to claim 23 wherein the connector block remains in contact with its seal tray when the access openings of the connector block are in communication with the port, to hold the seal tray in position on the lid.

26. The system according to claim 22 further comprising a first block, slidably mounted in the track, the first block being initially aligned with the port, but being displaceable by the connector block, and wherein the rack-and-pinion lever means for moving the connector block comprises a lever, having a pinion engaging at least one of the first block and the connector block, for moving the first block and the connector block when the pinion rotates as the lever is pivoted.

27. The system according to claim 26 wherein the pinion includes a toothed pinion, and wherein at least one of the first block and the connector block has a toothed rack adapted to be engaged by the pinion such that rotation of the pinion caused by the pivoting of the lever moves the first block and the connector block.

28. The system according to claim 26 further comprising means for releasably connecting the connector block and the first block, so that the connector block and the first block move together in the track.

29. The system according to claim 28 further comprising means for releasably locking the lever in position to secure the first block and the connector block in position on the lid.

30. A connection system for facilitating connections with a blood handling apparatus, to adapt the blood handling apparatus for a particular medical use, the system comprising:

a lid for the blood handling apparatus, the lid having at least one port which comprises at least one opening communicating with the blood handling apparatus;

a track for movably mounting one or more blocks on the lid, so that the blocks on the base can be aligned with the port and moved out of alignment with the port;

a first block mounted on the track in alignment with the port;

at least one connector block, each connector block having at least one access opening for communicating with the port in the lid, and at least one connection device for making a connection to the connector block to adapt the blood handling apparatus for a particular medical use when the connector block is in communication with the blood handling apparatus;

a seal tray for movably mounting each connector block and initially sealing the connector block's access openings, the seal tray and the connector block being configured so that the seal tray can be aligned with the track to allow the connector block to be moved at least partially off of the seal tray in the track, to bring the connector block's access openings into alignment with the port; and rack-and-pinion lever means for moving the first block out of alignment with the port means and for moving the connector block from the seal tray aligned with the track, at least partially off of the seal tray and into the track to bring the connector block's access openings into alignment with the port.

31. The system according to claim 30 wherein the rack-and-pinion lever means for moving the connector block comprises a lever, pivotally mounted on the lid, which engages at least one of the first block and the connector block, to move the first block and the connector block when the lever is pivoted.

32. The system according to claim 30 wherein the connector block is releasably attachable to the first block, and wherein the rack-and-pinion lever means for moving the first block and the connector block comprises a lever, pivotally mounted on the lid, which engages the first block to move the first block, and thus the connector block, when the lever is pivoted.

33. The system according to claim 30 wherein the lever includes a toothed pinion, and wherein the first block has a toothed rack adapted to be engaged by the pinion such that rotation of the pinion caused by the pivoting of the lever, moves the first block, and thus the connector block.

34. The system according to claim 33 further comprising means for releasably locking the lever in position to secure the first block and the connector block in position on the base.

35. A connection system for facilitating connections with a blood handling apparatus, to adapt the blood handling apparatus for a particular medical use, the system comprising:

a lid for the blood handling apparatus, the lid having at least one port which comprises at least one opening communicating with the blood handling apparatus;

a track for movably mounting one or more blocks on the lid, so that the blocks on the lid can be aligned with the port and moved out of alignment with the port;

at least one connector block, each connector block having at least one access opening for communicating with the port in the lid, and at least one connection device for making a connection to the connector block to adapt the blood handling apparatus for a particular medical use when the connector block is in communication with the blood handling apparatus;

a seal tray for movably mounting each connector block and initially sealing the connector block's access openings, the seal tray and the connector block being configured so that the seal tray can be aligned with the track to allow the connector block to be moved at least partially off of the seal tray in the track, to bring the connector block's access openings into alignment with the port; and a rack-and-pinion lever means for moving the connector block from the seal tray aligned with the track, at least partially off of the seal tray and into the track to bring the connector block's access openings into alignment with the port.

36. The system according to claim 35 further comprises a first block slidably mounted on the track; the rack-and-pinion means comprises:

a rack mounted on the first block;

a lever, pivotally mounted on the lid, for movement between a first position, in which the first block held in alignment with the port, and a second position, in which the connector block is held in alignment with the port; and a pinion mounted on the lever and in non-slipping engagement with the rack such that pivoting of the lever also pivots the pinion to move the rack, thereby to move the first block and connector block.

37. The system according to claim 36 wherein the connector block is releasably attachable to the first block so that, as the lever is pivoted to move the first block, the connector block is also moved.

38. The system according to claim 36 further comprising means for releasably locking the lever in the first and second positions to secure either the first block or the connector block in alignment with the port.

39. The system according to claim 38 wherein the means for releasably locking the lever comprises first and second means, each having a recess, for releasably receiving a portion of the lever to releasably hold the lever in its first and second positions, respectively.

40. The system according to claim 39 wherein the first and second means includes means for preventing overpivoting of the lever beyond the first and second positions.

41. The system according to claim 39 wherein the first and second means comprises first and second tabs extending from the base and defining the lever-receiving recesses, each of the first and second tabs having a sloped front portion on one side of the recess to cam the latch over the tab and into the recess, and a projection on the other side of the recess to prevent overpivoting of the lever beyond the recess.

42. The system according to claim 38 further comprising means for providing an audible and tactile indication when the lever is moved into either of its first and second positions.

43. The system according to claim 36 further comprising:

first and second outlets mounted on the reservoir; and valve means, operatively linked with the lever, for allowing drainage through the first outlet but not the second outlet when the lever is in its first position and allowing drainage through the second outlet but not the first outlet when the lever is in its second position.

44. The system according to claim 43 wherein the valve means comprises a generally cup-shaped member having a wall with an opening formed therethrough, and a shaft connecting the cup-shaped member to the lever such that pivoting the lever rotates the cup-shaped member to bring the opening of the cup-shaped member into alignment with the first outlet when the lever is in its first position and to bring the opening of the cup-shaped member into alignment with the second outlet when the lever is in its second position.

* * * * *